United States Patent [19]

Cahill et al.

[11] 4,238,628

[45] Dec. 9, 1980

[54] POLYALKYLAROMATICS UNDEGRADED DURING ALKYLATION

[75] Inventors: Paul J. Cahill, Wheaton, Ill.; Carl E. Johnson, San Diego, Calif.

[73] Assignee: Standard Oil Company (Indiana), Chicago, Ill.

[21] Appl. No.: 946,501

[22] Filed: Sep. 28, 1978

[51] Int. Cl.³ .................. C07C 39/38; C07C 2/54; C07C 37/12

[52] U.S. Cl. .................. 568/736; 568/792; 585/511; 585/314; 585/313

[58] Field of Search .................. 260/671, 671 C; 568/792, 793, 736; 585/516, 314, 313, 511

[56] References Cited

U.S. PATENT DOCUMENTS

| | | | |
|---|---|---|---|
| 2,398,253 | 4/1946 | Rogers et al. | 568/792 |
| 2,655,544 | 10/1953 | McNutty et al. | 568/792 |
| 2,671,117 | 3/1954 | Kluge et al. | 568/793 |
| 2,986,588 | 5/1961 | Schramm | 260/683.15 E |
| 3,000,964 | 9/1961 | Milligan | 568/792 |
| 4,017,548 | 4/1977 | Petrille | 568/792 |
| 4,070,402 | 1/1978 | Karll et al. | 568/792 |

FOREIGN PATENT DOCUMENTS 1159368 7/1969 United Kingdom .................. 568/792

OTHER PUBLICATIONS

Pis'man et al., Neftekhimiya, vol. 12, 69 (1972).
Yur'ev, et al., Neftekhimiya, vol. 12, 82 (1972).
J. Org. Chem., vol. 30, 3286, Shaw et al. (1965).

*Primary Examiner*—Werren B. Lone
*Attorney, Agent, or Firm*—William H. Magidson; William T. McClain

[57] ABSTRACT

Process for the production of undegraded alkylated aromatic compounds by alkylating an aromatic compound with a $C_3$ or higher olefin polymer having terminal ethylene units.

5 Claims, No Drawings

POLYALKYLAROMATICS UNDEGRADED DURING ALKYLATION

This invention relates to a process for the production of aromatic compounds having one or more high molecular weight alkyl side chains useful as intermediates in the manufacture of fuel and lubricating oil additives and sulfonate detergents. More particularly, this invention relates to a process for producing undegraded alkylated aromatic compounds by alkylating an aromatic compound with a $C_3$ or higher olefin polymer having terminal ethylene units, which process is especially useful in the preparation of polyalkylphenols employed in the manufacture of dispersant type additives.

Dispersant or detergent additives are employed in fuels and lubricating oils to retard engine fouling. Deposits of sludge, lacquer, and resinous materials form on the surfaces of engine components as lubricating oils deteriorate under conditions of use and possibly have a deleterious effect on engine efficiency, operation, and useful life. Dispersant or detergent additives act to prevent accumulation of deposits by keeping the deposit forming materials suspended in the oil so that engine parts remain cleaner and operate more efficiently. The Mannich Reaction, which comprises a condensation of an hydroxyaromatic, an aldehyde, and an amine is commonly used to generate effective nonmetallic dispersant agents for lubricating oils. Products of the Mannich Reaction wherein the hydroxyaromatic used is an alkylphenol containing an alkyl substituent of molecular weight in the range of 300 to 3000 or higher are used for their dispersant and detergent effect in such oils.

Alkylation of hydroxyl aryl compounds to generate alkylphenols is discussed in U.S. Pat. Nos. 2,398,253; 2,655,544; 2,671,117; and British Pat. No. 1,159,368; the latter discussing alkylations using as alkylating agents polymers of $C_{50}$ or more. Inherent to the acidic catalysts required for the alkylation reaction is concurrent polymer degradation and fragmentation of the polymeric alkyl substituent on the phenol. Known alkylation catalysts normally used such as the various Bronsted acids, Lewis acids, and solid metal oxides, have different fragmenting effects on the alkylating hydrocarbon depending upon its size. Most catalysts have little effect on olefin alkylating agents of up to twenty carbon atoms (up to 280 $\overline{M}_n$) at appropriate temperatures, but severe fragmentation results where alkylating agents of higher molecular weights are used. The fragmentation does not appear to be selective with respect to the higher or lower molecular weight members of an alkylating agent comprised of a polymeric mixture predominantly of one type of isomeric unit. Polymeric alkylating agents are usually derived from propylene or butenes and those comprised predominantly of butenes are the most susceptible to fragmentation during the alkylation reaction. When polybutenes of 300 to 3000 $M_n$ and higher are used molecular weight degradation of either the olefin polymer or the substituted alkyl group occurs.

British Pat. No. 1,159,368 teaches that fragmentation of both the alkylating agent and alkyl substituent can be suppressed but not eliminated by use of specified reaction conditions. These conditions comprise use of borontrifluoride-phenolate as the acidic catalyst within a temperature range of 0° to 65° C., with 0.1 to 1.1 mole borontrifluoride and from 1 to 4 moles of phenol per mole of mono-olefinic polymeric alkylating agent (molecular weight 700 to 300,000). Under the preferred conditions however the fragmentation of polybutenes can only be restricted at best to a level of about a 10% reduction of average molecular weight. Generally conditions must be chosen in accordance with practical demands and the level of degradation that can be tolerated for a specific application.

The degraded polyalkylphenols produced when polybutenes are employed in alkylation reactions are regarded as undesirable raw materials for the preparation of benzylamine dispersants by the Mannich Reaction. The dispersency properties require a crucial balance between the polar amine group and the oil solubilizing polymer group. The polymeric substituents of the alkylated phenol used as reactant influence the thermal stability and oil solubility of the dispersant generated. Therefore a process is needed for the production of alkylated aromatic compounds using polybutenes of 300 to 3000 $\overline{M}_n$ and higher as alkylating agents without polymer degradation or fragmentation of the polymeric alkyl substituent.

The condensation of olefins to form higher molecular weight olefins in the presence of alkali metals is a well known reaction. Generally the reaction is treated as proceeding via a carbanion mechanism wherein the alkali metal acts as a strong base and the olefin as a weak acid to form a metallic-organic intermediate. Appropriate reaction conditions and alkali metal catalysts for propylene dimerization are disclosed in U.S. Pat. No. 2,986,588, and the selectivity effects of the alkali metal catalyst on the product generated are discussed in Shaw et al., *J. Organ. Chem.*, 30, 3286 (1965). More recently studies have been conducted on the formation of by-product nonenes from this propylene reaction. The dimerization reactions of isobutylene and of isobutylene with ethylene and with propylene on metallic potassium have also been investigated. See Pis'man, et al., *Neftekhimiya*, 12, 69, (1972) and Yur'ev, et al., *Neftekhimiya*, 12, 82, (1972). Identification of individual components of the product mixtures obtained and elucidation of their structures is detailed but no use for the products is disclosed. Nor is reaction of polymers of 300 to 3000 $\overline{M}_n$ with propylene or ethylene suggested.

The general object of this invention is to provide an improved process for the production of intermediates useful in the manufacture of motor lubricant and fuel additives and of sulfonate detergents. Another object is to provide a process for the production of undegraded alkylated aromatic compounds, particularly polyalkylphenols, for use as Mannich reactants. A further object is to provide a process for alkylating aromatic compounds with a $C_3$ or higher olefin polymer without degradation of the polymer or of the polymeric alkyl substituent. Other objects appear hereinafter.

We have found that the objects of this invention can be accomplished by the alkylation of an aromatic compound with an alkylating agent comprised of a $C_3$ or higher olefin polymer having terminal ethylene units. Molecular weight degradation of the polyalkyl substituted aromatic through acid catalyzed depolymerization of the alkylating agent or fragmentation of the alkyl substituent is substantially avoided through use of this process.

The polymers contemplated as starting materials for the process include $C_3$ or higher olefin polymers of number average molecular weight of about 300 to about 6000. Preferred are polybutenes of $\overline{M}_n$ 300 to 3000 generated from an isobutylene rich refinery stream by polymerization in the presence of a suitable catalyst such as aluminum chloride. The polymer contains predominantly isobutylene units and is usually comprised of units derived from mono-olefins, with a minimum of 75% and preferably 85-95% of the units mono-olefinic, the balance of the units consisting primarily of isoparaffins. A minimal number of internal double bonds can occur. The olefin structure is predominantly the trisubstituted type with minor amounts of vinylidene and terminal vinyl structures present.

Suitable diluents can be used to reduce the viscosity of polymers to make them readily mixable and transferable by pumping operations and the like in the manufacturing facility. The amount used can vary over wide ranges. Commonly the diluent is used in such concentrations that achieve a suitable viscosity for the reaction mixture or product for ease of reaction and handling while not unnecessarily diluting the final product. Mineral lubricating oils are preferred if the ultimate product is an oil additive but diluents may be of synthetic, animal, vegetable, or mineral origin. Solvent extracted oils are desirable to avoid the presence of additives that could interfere with the desired reaction or generate side reactions. Specifically mineral oils of the grades from light white oils to solvent extracted SAE-40 are suitable. Diluents for polybutenes normally used in the present process include solvent extracted grades SAE-5 to SAE-10, preferably solvent extracted grade SAE-5.

Aromatics contemplated as reactants for alkylation with the olefin polymer include benzene and hydroxyl aryl compounds. Benzene is preferred when producing an intermediate for later use in the manufacture of sulfonate detergents, but hydroxyaromatics are employed when producing the alkylaromatic intermediates used in the Mannich Reaction to generate fuel and lubricating oil additives. A mononuclear monohydroxy aromatic such as phenol is preferred, but polynuclear hydroxy aromatics such as naphthol can be used. Substituents other than the hydroxyl group on the aromatic ring are not desirable.

A wide variety of alkylation catalysts are recognized and the particular catalyst chosen for a reaction is dependent upon the specific reactants used and end products desired. The alkylation of phenol with polymers of $\overline{M}_n$ 300 to 3000 is preferably catalyzed by borontrifluoride, and as previously mentioned, British Pat. No. 1,159,368 teaches that use of borontrifluoride complexed with phenol under specified reaction conditions will help suppress the fragmentation and depolymerization that result in degraded polyalkylphenols.

In somewhat greater detail undegraded polyalkyl substituted hydroxyaromatics can be produced by alkylating an hydroxyaromatic such as phenol with a $C_3$ or higher olefin polymer, preferably polybutene, stabilized through reaction with ethylene. Polybutene is first reacted with ethylene under pressure with heating in the presence of an alkali metal catalyst to generate a polymer of substantially the same molecular structure with terminal ethylene units. This polymer then serves as an alkylating agent to alkylate phenol in the presence of a borontrifluoride catalyst, yielding nearly undegraded polyalkylphenols. Polyalkylphenols prepared in a like manner with polybutene without terminal ethylene units undergo molecular weight degradation due to the concurrent depolymerization reaction.

A base catalyst is used to effect the reaction between the olefin polymer and ethylene by which stabilization of the polymer is attained. Appropriate catalysts include alkali metal catalysts such as sodium, sodium on charcoal, potassium, potassium on charcoal, sodium hydride, potassium hydride, and the like. Sodium on charcoal is preferred, and is prepared by heating molten sodium metal with powdered activated charcoal in a dry inert atmosphere such as nitrogen. An excess of charcoal is employed, with a preferred molar ratio of sodium to charcoal of about 1 to 5. Heating is continued for 20 minutes to an hour, preferably for one half hour, at 230°-330° C.

To effect the reaction of polybutene with ethylene, the polybutene is contacted in an autoclave reactor with ethylene gas in the presence of the sodium on charcoal catalyst, prepared as previously described, in a dry inert atmosphere such as nitrogen. After pressurization of the reactor with ethylene gas to the desired level, heat is applied to the system with stirring to generate contact and initiate the reaction. A mole ratio of polybutene to ethylene of 1 to 1 is preferred, although lower ratios are acceptable because the time available for adding the ethylene gas is limited by the fast reaction time.

Initial pressures of 500-800 psig of ethylene are suitable with a range of 600-700 psig preferred in the polybutene-ethylene reaction. Uptake of ethylene begins almost immediately upon pressurization and stirring at about 40° C. and the reaction is substantially completed during the first half hour. When a temperature of about 120° C. is obtained the reaction pressure is permitted to equilibrate with final pressures usually ranging from 200 to 600 psig, 400 to 600 psig most commonly occurring. One to three hours is normally required for reaction completion and equilibration.

The reaction of polybutene and ethylene is conducted at temperatures from about 35° C. to 150° C. Reaction begins at about 40° C. and heat is applied to obtain a preferred final temperature of 120° C., although final temperatures of 110° C.-140° C. are acceptable. The additional heat is utilized to assure reaction completion but does not substantially affect the rate of reaction.

After the system equilibrates pressure is vented and the product polymer is recovered by cleaning the reactor with a saturated or other inert hydrocarbon. Hexane is normally used but other suitable alkanes include those of $C_5$-$C_{10}$ such as pentane or decane. The catalyst is separated from the desired polymer by filtration or other appropriate means of separating solids from liquids such as by centrifugation, decantation, and the like, and the filtrate is then condensed under an inert gas such as nitrogen at the boiling point of the solvent. The condensed residue is dried by heating at this temperature to obtain the desired polymer with terminal ethylene units.

Yields of about 50%-70% of the product polymer are normally obtained. Comparison of nuclear magnetic resonance spectra and of olefin substituent analysis data of reactant and product polymers indicates that no major structural modification occurs during the reaction. The ethylated polymers obtained have substantially the same molecular structure as the initial polymers, implying that the olefin bond is not destroyed in the reaction. The polybutene reactant therefore can be selected in accordance with the polyalkyl substituent desired on the alkylated aromatic since no substantial change in the compound occurs during the addition reaction.

The severity of reaction conditions required appears to depend upon the particular polymer and catalyst employed. Reaction of polybutenes of varying molecular weight (300-3000) with ethylene over sodium on charcoal is easily initiated at about 40° C. upon pressurization at about 600 psig ethylene as described above. The similarly effected reaction of propylene tetramer with ethylene over sodium on charcoal initiates at about 130° C. and 800 psig of ethylene and requires approximately five hours for completion. The reaction of a lower molecular weight compound such as isobutylene with ethylene over potassium has been reported at 150° C. and 2200 psig. The ease of initiation and fast completion time of the polybutene-ethylene reaction are therefore an advantage in preparing polybutenes that can be used as alkylating agents without degradation to generate intermediates of the desired molecular weight range useful in the Mannich Reaction.

The polybutene polymer with terminal ethylene units is then used to alkylate phenol using a borontrifluoride catalyst. The catalyst is preferably complexed with the phenol prior to reaction with the polymer to generate borontrifluoride phenolate which aids in suppressing fragmentation and which also provides the convenience of a liquid system for control and storage in the manufacturing facility. The complex is prepared by adding borontrifluoride gas to a liquid form of phenol, either molten phenol or a solution of phenol in an alkane or light mineral oil, in an amount necessary to provide the phenol to borontrifluoride ratio desired for the alkylation reaction. Suitable solvents for the phenol include $C_5$-$C_8$ alkanes such as pentane or octane and solvent extracted oils of grades SAE 5 to SAE 10. The mole percent of borontrifluoride in the complex is preferably 10% but can range from 5% to 30%.

The phenol catalyst complex is added with stirring to a conventional reactor of glass or borontrifluoride resistant metal containing the polymer over an interval of approximately five minutes. The rate of addition does not materially affect the efficiency of the alkylation reaction so can be decreased if necessary to control any temperature rise. The preferred mole ratio of phenol catalyst complex to polymer varies with the molecular weight of the polymer. For polymers of molecular weight of about 300–1500 the mole ratio of complex to polymer can range from 1:1 to 2:1 with 1.5:1 being preferred. For polymers of higher molecular weight of about 1500–3000 a complex to polymer mole ratio of 2.7:1 is preferred but it can vary from 2:1 to 3:1. The preferred ratios are based on consideration of concentration of olefin in the polymer, dilution of polymer and catalyst complex necessitated by viscosity, reactivity rate desired for a given manufacturing facility, and conditions active in suppressing fragmentation.

Control of temperature within the range of about 45° C. to 55° C. is desirable although the alkylation reaction can be conducted at from about 0° C. to 60° C. Temperatures above 60° C. usually result in degraded alkylphenols. The reaction is relatively nonexothermic due to the low olefin concentration of the polymers. Polybutenes with terminal ethylene units at the lower end of the 300 to 3000 $\overline{M}_n$ range yield nonexothermic mixtures upon alkylation even when their counterparts without ethylene groups can form an exothermic reaction mixture. Excessive temperature can be controlled by lengthening the period of addition time of the phenol catalyst complex to the polybutene and by cooling of the reaction mixture.

The alkylation reaction proceeds at atmospheric pressure. Formation of slightly greater pressures when using a closed system is permissible but does not increase the reaction rate. The reaction mixture is stirred throughout the alkylation and stirring is commonly continued for a minimum of two hours to assure reaction completion.

The borontrifluoride catalyst is preferably neutralized by precipitating it with ammonia. Any unreacted phenol is then separated from the reaction mixture by stripping with an inert gas such as nitrogen applied at a rate of about four cubic feet per hour for approximately two hours at 225°–240° C. The stripping also tends to aid in agglomeration of the insoluble borontrifluoride precipitate. The precipitated catalyst is then separated from the desired polyalkylphenols by filtration or other suitable means of separating solids from liquids.

The alkylation reaction yields primarily monoalkylated phenol with substitution predominantly para to the hydroxyl group. This is in accordance with the para directing effect previously documented of borontrifluoride phenolate catalysis in the alkylation of phenols. Molecular weight data for alkylphenols generated from polymers with terminal ethylene units and their counterparts without terminal ethylene units shows significant differences. Analysis of the polyalkylphenols generated from the polymers reacted with ethylene shows that nearly undegraded polyalkylphenols are prepared. The terminal ethylene units stabilize the polymer in alkylation reactions and minimize depolymerization of the alkylating agent and fragmentation of the alkyl substituent promoted by the acidic alkylation catalyst. Thus molecular weight degradation of polybutenes of $\overline{M}_n$ 300 to 3000 in alkylating phenol can be substantially avoided by use of this process wherein polybutenes with terminal ethylene units are employed. The alkylated phenols generated contain the high molecular weight side chains desirable for use in the Mannich Reaction to prepare dispersant additives for fuels and lubricating oils.

EXAMPLE 1

Three tenths of a mole (600 g) of polybutene of $\overline{M}_n$ 2366 was charged to a one liter autoclave reactor containing a sodium on charcoal catalyst previously prepared by heating six grams of sodium metal with thirty grams of activated charcoal under nitrogen at 230°–315° C. for one half hour. The reactor was sealed and pressurized to 600 psig with ethylene. Heat was applied to the system with stirring and reaction began almost immediately at about 38° C. After 1.75 hours the system was equilibrated at 120° C. and 420 psig, pressure was then vented, the reactor was cleaned with hexane and the catalyst was separated by filtration of the hexane suspension. The product polymer was recovered by condensation of the filtrate under nitrogen. A twenty five gram sample of the condensed residue was heated in vacuo four days at 65° C. to approximately constant weight for use in nuclear magnetic resonance and associated olefin analyses. These analyses were performed on reactant and product polymers to elucidate the structure of the latter. Resulting data showed no major structural modification of the polybutene occurred during the reaction. The mole percent of disubstituted olefin was 23% in the product polymer compared to 24% in the polybutene raw material. Although a larger difference in mole percent of trisubstituted olefin was obtained of 31% in the product polymer versus 50% in the reactant, it was attributed to the lack of sensitivity of the analysis since olefin concentration is low in such polymers and the nuclear magnetic resonance spectra showed no major change in the olefin pattern. This example illustrates the reaction of polybutene with ethylene to produce a polymer with terminal ethylene units.

EXAMPLES 2 AND 3

These examples illustrate use of lower molecular weight polybutenes in the reaction of Example 1. Ethylene was reacted with polybutenes of $\overline{M}_n$ 1016 and 320 by the method of Example 1 except that the proportion of reactant and equilibration temperatures and pressures where as shown in Table I. Data from the analyses of the resulting product polymers is shown in Table II and indicates that the reaction is effective in producing polymers of substantially the same structure for polybutenes of lower molecular weights.

Table I

|  | Reactants | |
| --- | --- | --- |
|  | Polybutene ($M_n$ 1016), 500g Ethylene, 33g Sodium, 6g Charcoal, 30g | Polybutene ($M_n$ 320), 400g Ethylene, 42g Sodium, 6g Charcoal, 30g |
| Initial Temp. °C. | 43° | 38° |
| Initial Pressure, psig | 700 | 700 |
| Final Temp. °C. | 129° | 121° |
| Final Pressure, psig | 460 | 480 |
| Reaction Time, hrs | 1.9 | 2.0 |

Table II

| Polymer | Mole % Disubstituted Olefin | Mole % Trisubstituted Olefin |
| --- | --- | --- |
| Polybutene ($\overline{M}_n$ 1016) +Ethylene | 8.5% | 53.1% |
| Polybutene ($\underline{M}_n$ 1016) | 10.1% | 55.2% |
| Polybutene ($M_n$ 320) +Ethylene | 7.3% | 58.4% |
| Polybutene ($M_n$ 320) | 8.0% | 66.2% |

EXAMPLES 4 AND 5

These examples illustrate the alkylation of phenol with polybutenes having terminal ethylene units to generate polybutylphenols substantially undegraded by concurrent depolymerization of the reactant polymer or fragmentation of the alkyl substituent. Borontrifluoride gas was bubbled through molten phenol in a two liter glass reactor to generate a borontrifluoride phenolate complex containing ten mole percent borontrifluoride. The complex was slowly added over a five minute interval at 45° C. to four individual two liter glass reactors containing respectively (1) polybutene of $M_n$ 1016 with terminal ethylene units generated in Example (2, 2) polybutene of $\overline{M}_n$ 1016 used as reactant in Example (2, 3) polybutene of $\overline{M}_n$ 2366 with terminal ethylene units in solvent extracted SAE-5 diluent generated in Example (1, 4) polybutene of $\overline{M}_n$ 2366 in solvent extracted SAE-5 diluent used as reactant in Example 1. Mole ratios of 2.7:1 complex to polymer was used for polybutenes of $M_n$ 2366 and of 1.5:1 complex to polymer for polybutenes of $\overline{M}_n$ 1016. The reactors were heated with stirring to a temperature of about 55° C. and stirring thereafter was continued for two hours. The catalyst was neutralized by precipitation with ammonia and unreacted phenol was stripped out by nitrogen applied at a rate of four cubic feet per hour for two hours at 225°–240° C. The catalyst was removed by filtration, and activities of the filtrate were determined by silica gel chromatography and molecular weights by osmometry in benzene. Resultant data, shown in Table III, shows nearly undegraded alkylphenols were prepared.

Table III

| Polymer | Alkylphenol Activity | Alkylphenol Molecular Weight |
| --- | --- | --- |
| Polybutene ($M_n$ 2366) + Ethylene from Example 1 | 43.7% | 2415 |
| Polybutene $M_n$ 2366 (Example 1 reactant) | 44.8% | 1948 |
| Polybutene ($M_n$ 1016) + Ethylene from Example 2 | 64.1% | 1190 |
| Polybutene ($M_n$ 1016) (Example 2 reactant) | 62.4% | 1056 |

EXAMPLE 6

Polybutene ($\overline{M}_n$ 2366) with terminal ethylene units generated in Example 1 was used to alkylate phenol by the method of Examples 4 and 5 except that an alkylbenzene sulfonic acid was added to the catalyst system in an amount comprising 0.4% of the reaction mixture to serve as a buffering agent for the alkylation reaction. No adverse effects were observed and the resultant alkylphenol had an activity of 44.9% and a molecular weight of 2480.

EXAMPLE 7

Polybutene ($\overline{M}_n$ 1016) with terminal ethylene units generated in Example 2 was used to alkylate phenol by the method of Examples 4 and 5 except that the alkylation reaction was conducted at a temperature of 65°–70° C. A degraded alkylphenol with an activity of 44.6% and a molecular weight of 888 was obtained. This example illustrates that normal alkylation temperatures cannot be exceeded when using the process of this invention.

We claim:

1. A process for the production of undegraded alkylated benzene, phenol, and naphthol compound comprising alkylating, at about 0° to 60° C., a complex comprising boron trifluoride and benzene, phenol, or naphthol with a $C_3$ or higher olefin polymer having terminal ethylene units, wherein the molar ratio of complex to olefin polymer is about 1:1 to 3:1.

2. The process of claim 1 wherein the $C_3$ or higher olefin polymer having terminal ethylene units is a polybutene having terminal ethylene units.

3. The process of claim 2 wherein the polybutene component of the polybutene having terminal ethylene units has an average number of molecular weight of about 300 to 3000.

4. The process of claim 1 wherein the complex comprises boron trifluoride and phenol.

5. The process of claim 2 wherein the complex comprises boron trifluoride and phenol.

* * * * *